United States Patent [19]

Bazin

[11] Patent Number: 5,858,359
[45] Date of Patent: Jan. 12, 1999

[54] ANTIBODIES FOR AND TREATMENT TO PREVENT OR REDUCE THE SEVERITY OF XENOGRAFT REJECTION

[76] Inventor: Herve Bazin, 120 Avenue Marie-Jose, Brussels 1200, Belgium

[21] Appl. No.: 424,293

[22] PCT Filed: Mar. 1, 1993

[86] PCT No.: PCT/US93/01743

§ 371 Date: Apr. 17, 1995

§ 102(e) Date: Apr. 17, 1995

[87] PCT Pub. No.: WO93/16729

PCT Pub. Date: Sep. 2, 1993

Related U.S. Application Data

[63] Continuation-in-part of Ser. No. 843,608, Feb. 28, 1992, abandoned.

[51] Int. Cl.$^6$ .......................... A61K 39/395; C07K 16/42
[52] U.S. Cl. ..................................... 424/130.1; 424/141.1; 424/152.1; 424/158.1; 530/388.73
[58] Field of Search .............................. 424/130.1, 141.1, 424/145.1, 152.1, 172.1, 173.1, 153.1, 158.1; 604/5, 6; 210/140.1, 130.1, 141.1, 152.1, 158.1, 690, 691; 530/388.73

[56] References Cited

U.S. PATENT DOCUMENTS 4,863,869  9/1989  Balint ...................................... 435/296

OTHER PUBLICATIONS

Nowak, R. Science. 266:1148–1151, Nov. 1994.
Harris, WJ and Emery S. TIBTECH. 11: 42–44, Feb. 1993.
Johnston, PS et al. Transplantation. 54(4): 573–576, Oct. 1992.
Fischel, RJ et al. Transplanation Proceedings. 22(3): 1077–1078, Jun. 1990.
Schwartz, RS and Datta, SK. Autoimmunity and Autoimmune Diseases. in: Fundamental Immunology: Second Edition. WE Paul, ed. Raven Press, New York. pp. 819–866, 1989.

*Primary Examiner*—David Saunders
*Assistant Examiner*—F. Pierre VanderVegt
*Attorney, Agent, or Firm*—Jacobson, Price, Holman & Stern, PLLC

[57] ABSTRACT

Anti-human IgM antibody; in particular, an anti-human mu chain antibody can be employed for reducing patient levels of natural antibodies which are xenoreactive to eliminate or reduce the severity of xenograft rejection.

5 Claims, 9 Drawing Sheets

ANTIBODIES FOR AND TREATMENT TO PREVENT OR REDUCE THE SEVERITY OF XENOGRAFT REJECTION

This application is a National Stage under 35 U.S.C. § 371 of PCT/US93/01743, filed Mar. 1, 1993, which is a continuation-in-part of U.S. application Ser. No. 07/843,608, filed Feb. 28, 1992, now abandoned.

This invention relates to xenograft transplants and more particularly to antibodies and a process for treating a patient to prevent or reduce the severity of xenograft rejection.

As a result of shortages of organs, tissues and cells which are available from humans for transplantation purposes, there have been numerous proposals to obtain organs, tissues and cells from nonhuman animals for transplantation into humans.

As in transplantation procedures involving transplantation of organs from one human to another human, rejection of the nonhuman organ is a serious hurdle to the effective use of xenografts.

It is believed that preformed natural antibodies present in humans are one of the principal causes of xenograft hyperacute rejection. As a result, there have been numerous proposals for removing such preformed natural antibodies.

One such proposal is plasma exchange; however, such technique suffers from the disadvantage that all circulating antibodies and many other proteins are removed, whereby a patient loses many beneficial antibodies, as well as the natural antibodies.

Another proposal is the use of nonspecific absorbants (such as antibodies or naturally occurring substances which recognize the Fc region of an antibody) for removing immunoglobulins from plasma. As with plasma exchange, such a technique removes beneficial antibodies as well as natural antibodies which are believed to cause xenograft or ABO incompatible allograft rejection.

Another method which has been proposed is the use of specific materials for removing the specific natural antibodies which are believed to cause xenograft rejection. Such proposal would involve removal of the natural antibodies against the species which is the source of the xenograft. Thus, for example, if an organ from a swine is to be transplanted into a human, in accordance with this proposal, a material would be used which would specifically remove human anti-swine antibodies. Although such a proposal is theoretically possible, to date, the feasability of such technique has not been demonstrated.

Another method which has been proposed is the use of an antigen which complexes with the antibody against the xenograft, whereby such antibody is no longer free to bind with antigen sites on a xenograft. The resulting complex, however, could potentially have detrimental effects.

As a result, there is a need for new and improved methodology for treating patients to prevent xenograft rejection.

In accordance with an aspect of this invention, there is provided an anti IgM antibody and more particularly an anti-human IgM antibody.

In accordance with another aspect of the present invention, an anti-human IgM antibody is used to lower the levels of natural antibodies which react with a xenograft in a patient who has or is to receive a xenograft.

More particularly, the use of anti-human IgM antibody reduces the level of natural antibodies which react with a xenograft to cause xenograft rejection or ABO allograft rejection, without eliminating beneficial non-IgM antibodies.

The natural antibodies which result in xenograft rejection are mainly of the IgM class whereby the use of an anti-human IgM antibody will lower blood levels of the natural antibodies which are xenoreactive to thereby minimize or eliminate xenograft rejection or ABO allograft rejection.

In accordance with a further aspect of the present invention, the anti-human IgM antibodies are anti-human Mu chain antibodies which react with the mu chain portion of the constant region of human antibodies, with such mu chain being characteristic of an IgM antibody. Such anti-human IgM antibody may be used to lower the serum levels of IgM xenoreactive natural antibodies.

In accordance with still another aspect of the present invention, a patient is treated to prevent or reduce the severity of rejection of a xenograft from a non-human animal, such as swine by contacting the patients blood with an anti-human antibody which immunoreacts with human natural antibodies against a xenograft from such non-human animal. Thus, for example, an anti-human IgM antibody can be employed to reduce blood levels of natural human IgM antibodies against swine or any other non-human animal to permit transplantation of a swine organ or an organ from another non-human animal into a human.

As hereinabove indicated, the anti-human IgM antibody which is preferably employed in the present invention is one which is an anti-mu chain antibody; i.e., the antibody recognizes the mu chain which forms a part of the constant region of an IgM antibody. The antibody which is employed, may be a polyclonal antibody or a monoclonal antibody. The antibody may also be employed as a single chain antibody, or as an antibody fragment which recognizes the mu chain of an anti-human IgM antibody. The term "antibody" as used herein includes polyclonal and monoclonal antibodies, as well as antibody fragments, and antibodies prepared by recombinant techniques, such as chimeric or humanized antibodies, single chain antibodies and whole antibodies made by recombinant techniques.

A monoclonal antibody may be produced by techniques generally known in the art and in particular, the technique disclosed. The preparation of a monoclonal anti-human IgM antibody is described in more detail in Example 1 of the present application. The monoclonal antibodies can be from a variety of species; for example, mouse monoclonal antibodies, rat monoclonal antibodies, etc. Such antibodies for IgM are also described in Rat Hybridomas and Rat Monoclonal Antibodies, Chapter 19, VI (CRC Press). A polyclonal antibody which is an anti-human IgM antibody may also be produced by techniques generally known in the art.

As hereinabove indicated, anti-human IgM antibody may also be produced by recombinant techniques using procedures known in the art. The recombinant antibody may also be in the form of a chimeric antibody wherein the variable or CDR region of an anti-human IgM antibody of one species is combined with the constant region of an antibody of another species. Thus, for example, the variable or CDR portion of a murine anti-human IgM antibody may be combined with the constant region of a human antibody to provide a chimeric anti-human IgM antibody.

The preparation of anti-human IgM antibody suitable for the purposes of the present invention should be apparent to those skilled in the art from the teachings herein.

As hereinabove indicated, anti-human IgM antibody may be employed in accordance with the present invention to reduce blood levels of xenoreactive natural antibodies. Such reduction may be accomplished by contacting whole blood or serum of a human patient with the anti-human IgM antibodies, and such procedure may be either an in vivo or ex vivo procedure.

Thus, for example, in an in vivo procedure, such anti-human IgM antibodies are administered to a patient in an amount effective to reduce blood levels of xenoreactive IgM natural antibodies to thereby reduce or eliminate xenograft rejection.

In such an in vivo technique, the anti-human IgM antibody is administered in a pharmaceutically acceptable carrier. As representative examples of such carriers, there may be mentioned normal saline solution, buffers, etc. Such pharmaceutical carriers are well known in the art and the selection of a suitable carrier is deemed to be within the scope of those skilled in the art from the teachings contained herein.

The anti-human IgM antibody may be administered in vivo intravenously, intramuscularly, etc.

As hereinabove indicated, anti-human IgM antibody is administered in vivo in an amount effective to reduce blood levels of IgM xenoreactive natural antibodies and in particular, natural IgM antibodies which are xenoreactive with swine antigen. In general, such antibody is administered in an amount of at least 25 mg. It is to be understood however that lower amounts could be used. For example, if there is a prior ex vivo treatment the in vivo treatment amounts can be reduced. In addition, after an initial treatment, the hereinabove described amounts may be reduced for subsequent treatments. Thus, the scope of the invention is not limited by such amounts.

In accordance with a preferred embodiment, such antibodies are repeatedly administered in order to reduce and preferably completely eliminate IgM xenoreactive antibodies. Thus, for example from 25–50 mg of such antibody may be administered in as a physiologically acceptable saline suspension every two days for a period of 14 days. Such treatment is preferably started at or immediately prior to the transplantation.

A patient may also be treated to reduce blood levels of xenoreactive antibodies by an ex vivo procedure. In such a procedure, blood or serum derived from a patient is treated in vitro by contact with the anti-human IgM antibody, and after such treatment, the treated blood is returned to the patient.

Thus, for example, anti-human IgM antibody may be supported on a suitable solid support and blood or serum derived from a patient is contacted with the supported antibody and returned to the patient.

Any one of a wide variety of solid supports may be employed for supporting the antibody in such an ex vivo treatment. Thus, for example, the support may be in the form of beads in a column, on a solid sheet and the like. Such techniques are generally known in the art, and should be apparent to those skilled in the art from the teachings herein.

The technique of the present invention for reducing blood levels of xenoreactive IgM natural antibodies may be employed alone or in combination with other techniques for reducing or eliminating xenoreactive IgM natural antibodies from a patient to prevent or reduce the severity of xenograft rejection.

Similarly, the removal of natural antibodies as herein described may be employed in combination with other techniques for eliminating or reducing the severity of xenograft rejection.

BRIEF DESCRIPTION OF THE DRAWINGS

FIG. 10 depicts complement C1q, C3 and C5 levels, showing that MARM7 did not decrease complement activity.

Figure 1A:
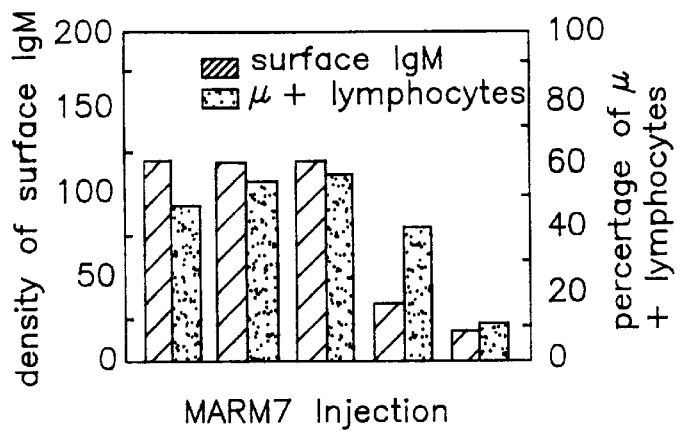
FIGS. 1a and 1b show the detection of membrane IgM in the surface of B lymphocytes.

The invention will be further described with respect to the following examples, which are illustrative and which do not limit the scope of the invention:

EXAMPLE 1

Preparation and production of LO-HM-7 Antibody

LO-HM-7 antibody is produced by immunization of a rat (LOU/C) with human IgM. Specifically, LO-HM-7 hybridoma were produced, using an in vivo system, as a result of the fusion of a non-secreting IR983F fusion cell line (1) and B lymphoblasts from LOU/c rats having a kappa-light chain allotype of IgK-1a.

Ascites were produced in congenic rats, LOU/C. IgK1b (OKA) which produced Kappa-light chain immunoglobulins of the IgK-1b allotype, to allow the separation of host and hybridoma immunoglobulins.

LO-HM-7 ascites were then produced by injecting subcutaneously 3–5×10$^5$ cells into 8 week old LOU/C.IgK1b rates. After 2–3 weeks, a piece of the developing solid tumor is excised and disrupted in PBS. Using the resulting PBS solution, 3–5×10$^6$ cells (approximately 2 ml in PBS) and 2 ml of incomplete Freund Adjuvant (Difeo) were injected intraperitoneally in 20 to 50 LOU/C.IgK1b rats. Fifteen days later the ascitic fluid was collected from each rat and pooled.

After collection and pooling the ascitic-fluid was immediately centrifuged (25,000 G, 15 minutes). 50 µl of PMSF (Sigma, 40 mg/ml in ethanol) and 20 µl of thimersol (Sigma, 1 g/ml) were added per ml of supernant. The Ig content of ascitic fluid supernatant was tested by agarose electrophoresis and kept at –20° C.

At least 1 liter of the ascitic fluid was thawed at 25° C. and centrifuged (25,000 G, 15 minutes). To remove lipids from the supernatant, it was diluted twice with DELIFREN MP (trichlotrifluoroetbone) (Monsanto), then shaken for 30 minutes, centrifuged (25,000 G, 15 minutes) and filtered through #4 Whatman filters.

The resulting sample was absorbed on a Mark-3 Immuno Affinity Column (Mark 3-Mouse Anti-Rat IgK-1b immunoglobulins). The material which remained unbound contained host Kappa 1b immunoglobulins and contaminent proteins, and as such was discarded.

The material bound to the column was eluted with 100 mM Glycine/HCR buffer (pH 3.50) containing 0.1M NaCl and neutralized with Tris-HCl buffer (1M pH 8.00). The sample was concentrated using Millipore's MINITAN or PELLICON from concentration system with membranes having a 30× cut-off and then diluted with PBS. The steps beginning with the sample being eluted from the column were repeated four times.

The removal of endotoxins was accomplished by eluting the sample through Q-Sepharose Fast Flow gel (flow rate 10 cm/h). Prior to using the gel it was santized with 0.1M NaOH and washed with a pyrogenic water and PBS.

For purposes of purity control samples were submitted to native PAGE (gradient 3–15% according to Laemmli) and scanned using GS300 Scanning Densitometer (Hoefer, San Francisco). The Scannings were monitored with GS365 software (Hoefer, San Francisco).

EXAMPLE 2

Balb/c mice were injected with rat IgM and the B lymphoblasts fused to SP20 fusion cell line.

Production of Marm-7 Ascites 0.3 ml of 6, 10, 14 Tetra-methyl-pentadecane was injected intraperitoneally in 10 weeks old (NMR2×BALB/C F) mice. Three weeks later, mice were irradiated (3 Gy). Then, $3-5\times10^5$ cells from the above hybridoma (1 ml in PBS) were injected intraparitoneally. The ascites fluid was collected 10 to 15 days later.

Preparation of the Ascitic Fluid

After harvesting, ascitic fluids were immediately centrifugated (25,000 c. 15 min.). 50 μl of PMSF (Sigma, 40 mg/ml in ethanol) and 20 μl of Thimerosal (Sigma, 1 g/ml) were added to 1 ml of supernatant. The Ig content of ascitic fluid was tested by agarose electrophoresis and kept at −20° C.

The ascitic fluid (at least 200 ml) was thawed at 25° C. and centrifuged (25,000 G. 15 min.).

To remove lipids, the supernatant was diluted twice with DELIFRAM MP (Monsanto), shaken for 10 minutes, centrifuged (25,000 G, 15 min.) and filtered on 4 whatman filters.

DEAE-SEPHAROSE 200 ml of sample were dialyzed 3 times against Tris-HCl buffer (0.05M; pH 8.00) and adsorbed on an anion exchange column (DEAE-Sepharose Fast Flow, Pharmacia; K-50 column; bed height: 30 cm) equilibrated with Tris-HCl buffer (0.05N; pH 8.00) at a flow rate of 10 ml/h.

Bound material was eluted with a Tris-HCl discontinuous gradient (buffer A: Tris-HCl 0.05M, pH 8.00; buffer B: Tris-HCl 0.05M, NaCl 0.2M, pH 8.00) at a flow rate of 5 ml/h. The peaks were tested for the antibody presence.

Sample was concentrated using Millipore's Minitan or Pellicon system with membranes having a 30K cut-off and then diluted with PBS. These steps were repeated four times.

Removing of Endotoxine (if necessary)

In order to remove endotoxins, sample was then eluted through Q-Sepharose Fast Flow gel (Flow rate 10 ml/h). The gel was first sanitized with 1N NaOH and washed with apyrogenic water and PBS.

Purity Control

Samples were submitted to native PAGE (gradient 3–15% according to Lamnli) and scanned using GS300 Scanning Densitometer (Hoefer, San Francisco).

The scannings were monitored with GS365 software (Hoefer, San Francisco).

Currently, the final purity is better than 60%.

EXAMPLE 3

MARM-7 antibody is produced by immunization of mouse with rat IgM more specifically the monoclonal antibody used is a mouse IgG1 anti rat mu chain; MARM-7. IgM and xenoreactive natural antibodies depletion from adult LOU/C rats sera was achieved by intraperitoneal injection of MARM-7.

In a dose response study, 0,1,2,5 or 10 mg of MARM-7 were intraperitoneally injected in 5 different rats. Treated animals were sacrified 24 H after injection and seric levels of IgM, MARM-7 as well as the expression of IgM on the surface of splenic and peripheral blood B lymphocytes were analysed.

Figure 1B:
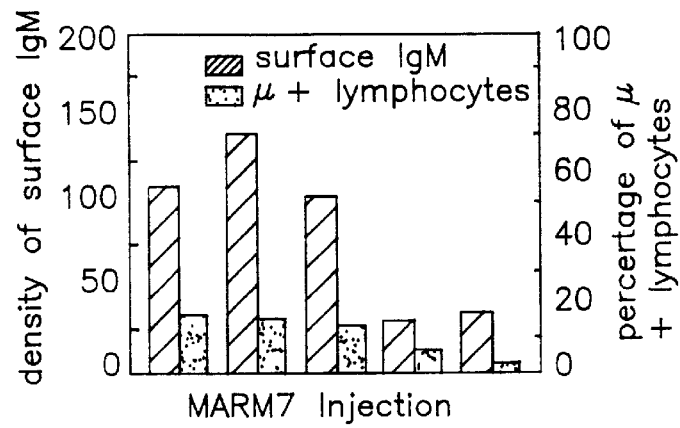

24 h after the injection of 10 mg of MARM-7, serum levels of IgM and anti guinea pig xenoreactive IgM natural antibodies were strongly decreased (99%). In parallel, high levels of free MARM-7 were detected in the serum of treated animals (400 μg/ml). On the other hand the percentage of IgM+ B splenic lymphocytes in those animals also decreased (from 60% to 10% in the spleen) (FIG. 1a and 1b) and the expression of IgM in the surface of these cells was very low compared to non-treated animals. Similar results were obtained for PBL B IgM+ cells. Neither 1,2 or 5 mg of injected MARM-7 gave similar results. So, in order to achieve the depletion of IgM serum levels and the internalisation of IgM from the surface of IgM+ B cells further experiments were made using doses of 10 mg of MARM-7.

Figure 2:
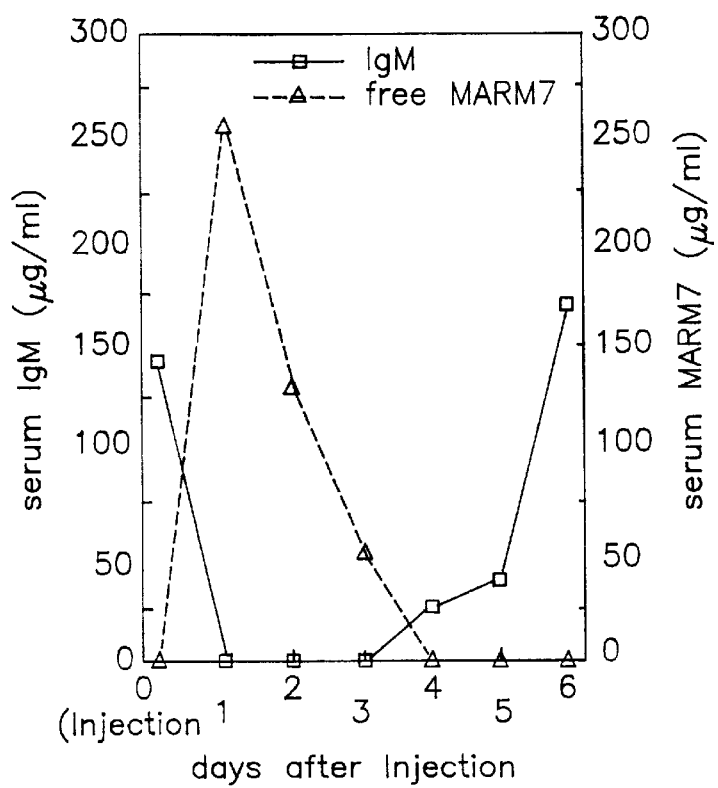
FIG. 2 shows the detection of IgM and free MARM7 after injection of MARM7 (day 0).

Time course analysis after injection of a single dose of 10 mg of MARM-7 showed that only a short term depletion (3 days) of serum IgM and xenoreactive IgM natural antibodies could be achieved by this treatment. The results obtained (FIG. 2) showed that as soon as free MARM-7 became non-detectable in treated rats sera (Days 3–4) IgM slowly reappears in the circulation to reach pre-treatment levels 6 days after MARM-7 injection.

Figure 3A:
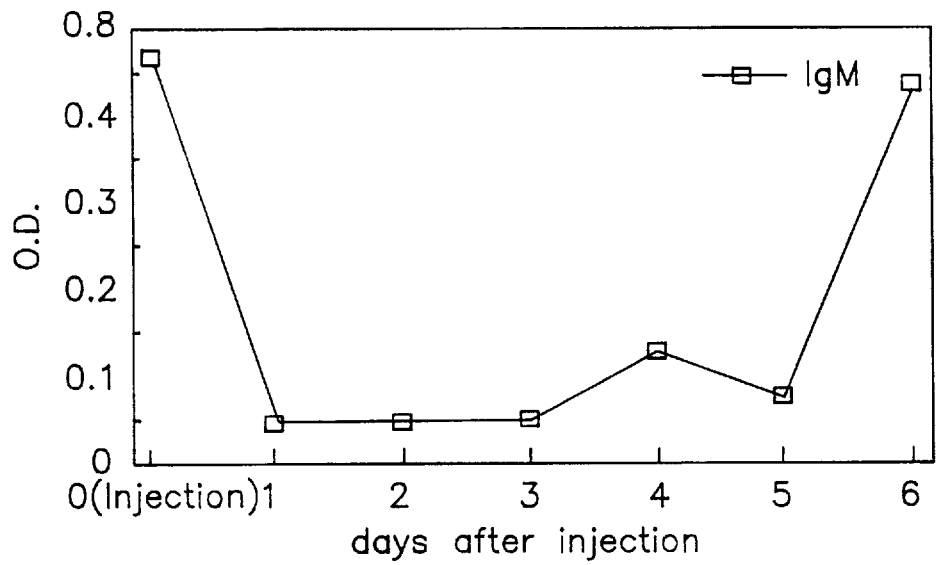
FIGS. 3a and 3b show the expression of IgM in the surface of splenic B lymphocytes after injection of 10 mg of MARM7.
Figure 3B:
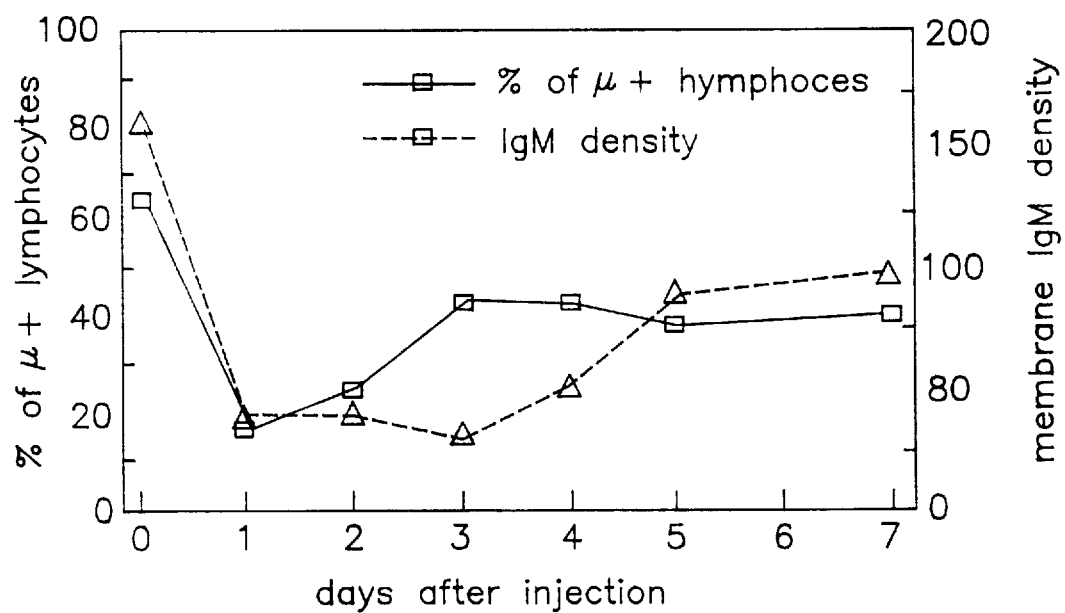

IgM expression on the surface of B splenic lymphocytes remained at a residual level for the 3 days (FIG. 3a and 3b) following the MARM-7 injections but as soon as free MARM-7 disappeared from the sera (days 3–4) B cells expressed IgM de novo reaching the pre-treated levels at day 7.

In order to achieve a long term depletion of serum IgM, 3 rats were injected with 10 mg of MARM-7 at day 0 followed by 5 injections of 5 mg of MARM-7 every 48 hours (days 2,4,6,8,10).

This sequential administration of anti rat IgM resulted in the complete depletion of IgM and anti guinea pig IgM xenoreactive natural antibodies for 30 days.

Figure 4:
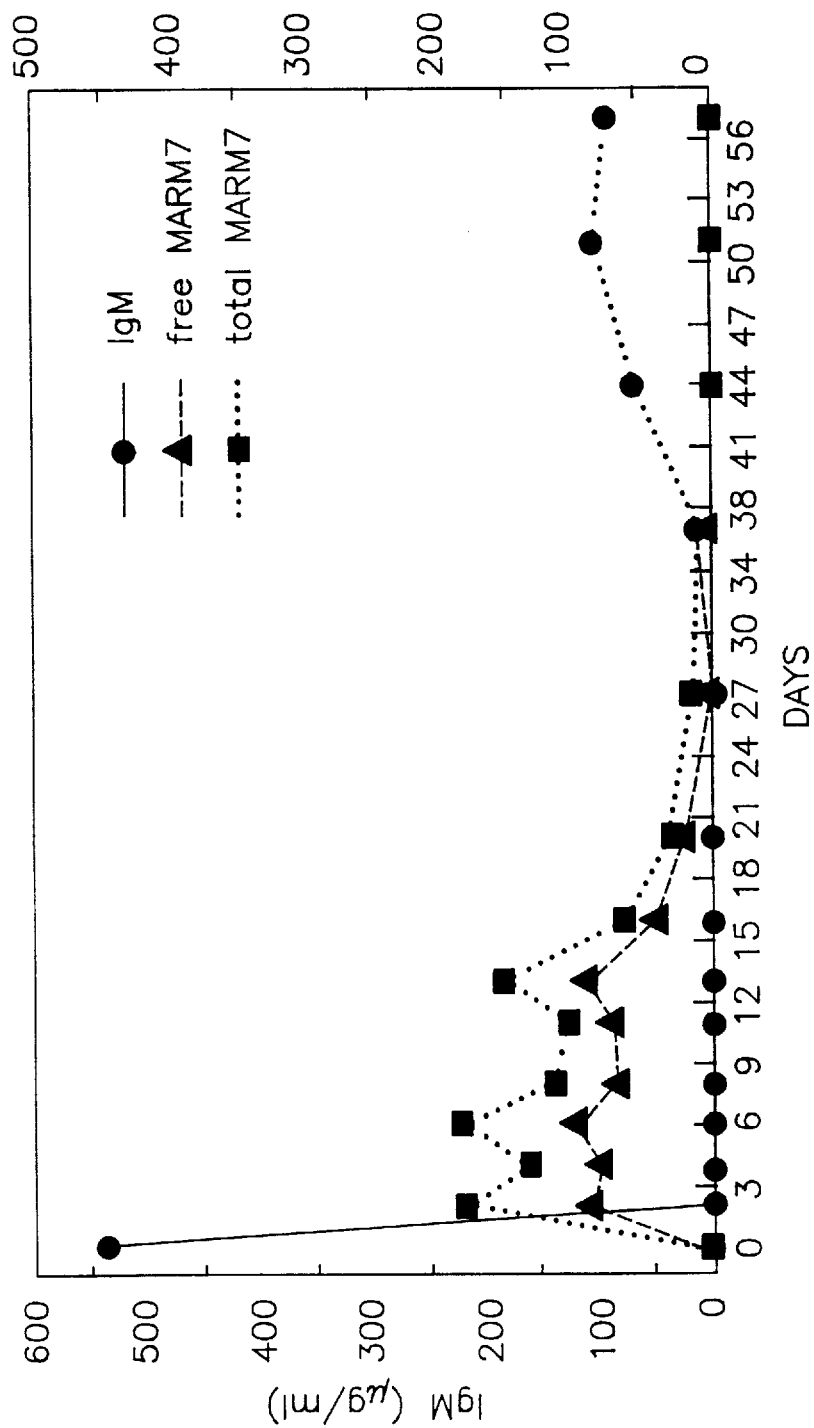
FIG. 4 shows the depletion of serum IgM by multiple injection of MARM7 in an adult rat.
Figure 5:
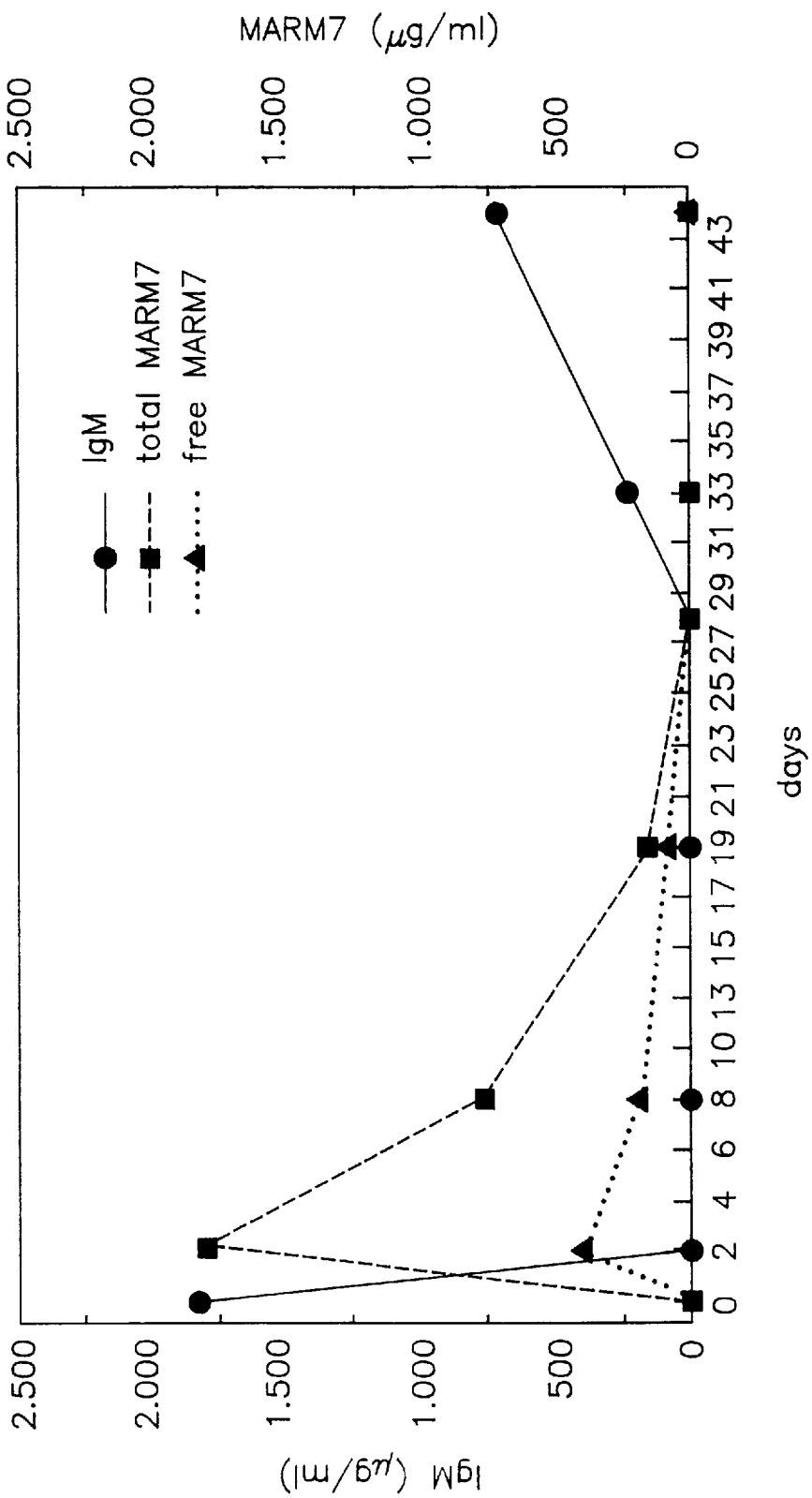
FIG. 5 shows the depletion of serum IgM by multiple injection of MARM7 in an adult rat.

The evolution of seric levels of IgM, total MARM-7 and free MARM-7 are shown on FIG. 4 and 5 in two representative treated LOU/C rats.

EXAMPLE 4

ANIMALS

Animals used as xenograft recipients were inbred male LOU/C rats, 1718 weeks old, body weight 267±23 g, bred in our animal house, kept under conventional clean laboratory conditions and fed ad libitum with commercial pellets. Animals used as xenograft donors were HartleyDunkin outbred male guinea pigs (janssen, Belgium), body weight 612±160 g, kept under conventional laboratory conditions and fed ad libitum. Male and female outbred guinea pigs (UCL, Belgium) were also used as source of endothelial cells in order to analyse rat antiguinea pig Igm and IgG2a XNA.

TRANSPLANTATION TECHNIQUE

Donor Operation

Cardiac xenografts were achieved as described by Heron (1974) and Olausson et al. (1984); briefly: Donor operation. Guinea pig abdomen was opened through a midline incision and 200 units of heparin (Liquemine, Roche,) were injected in the inferieur cava vein. The anterior thoracic cage was separated from the diaphragm, and the ribs were cut on both sides next to the middle-auxillary line to allow wide exposure. The cava and pulmonary veins were then ligated (3-0, Surgilon ligatures) and the heart was removed, flushed and stored in cold sterile saline solution until transplantation was achieved. The organ arterial supply was the aorta and the venous outflow was the pulmonary artery.

Recipient Operation

A skin incision was made on right anterolateral side of the rat neck. The sternocleidomastoid muscle was then resected and the right external jugular vein and right common carotid artery were dissected free and mobilized. Proximal portions of these vessels were occluded using microhemostat clips (Downs Surgical, UK) and distal portions ligated using 7-0 silk ligatures (B. Braun, Switzerland). Both vessels were irrigated through proximal cut ends using sterile saline solution. The extremities of the vessels were everted over the cuffs (8FG or 3PG) (Portex, UK) and ligated with a circumferential 7-0 silk ligature. The heart was then transferred to the neck of recipient, the guinea pig aorta and pulmonary artery were connected to the rat jugular vein and carotid artery cuffs, and secured by 7-0 silk ligatures. Surgical procedures were performed under anesthesia and under clean but not sterile conditions. Assessment of graft function. Xenocardiac graft function was assessed visually and by ECG registration (Hellige Servomed, SMK, 155-9, German6), using three electrodes placed over the xenotransplated heart. ECG was monitored from the time when the vascular clamps were released to the moment of heart beating cessation. Five to ten minutes after rejection, the xenograft was surgically removed and prepared for either conventional or immunohistological examination.

MONOCLONAL (MoAB) AND POLYCLONAL ANTIBODIES

MoAB anti-rat or mouse immunoglobulins. The nomenclature set of mouse anti-rat IG isotype is Mouse Anti-Rat Isotype and a number as for example MARK-1 for Mouse Anti-Rat kappa number 1. The one of rat anti-mouse Ig isotype is, Louvain Rat Anti-Mouse Isotype, and a number as for example LO-MG1-2 for Louvain rat anti-mouse IgG1 number 2. All MoAbs used in these experiment have been selected for their absence of cross-reactivities with other Ig isotypes of the same species at the concentrations used in our ELISA tests. More detailed information on these MoAbs can be obtained from the Hybridoma Data Bank (ATCC, USA; CERDIC, France; Riken, Japan). Their accession number are MARK-1, 230; MARM-4,7027; MARM-7,7030; MARG2a-1, still not attributed; LO-MG12,7138; LO-MG1-13, still not attributed; LO-DNP-34, 7087. These MoAbs are available from different firms such as Serotec, UK or Zymed Laboratories, USA. Highly purified rabbit anti-rat IgM or IgG2a polyclonal antibodies were used on immunochemistry assays in order to detected rat anti-guinea pig IgM and IgG2a XNAS. These polyclonal antibodies were depleted of all detectable rat isotype cross reactivity with other Ig isotypes of the same species by immunochromatography using sepharose 4b (Pharmacia, Sweden) coupled rat immunocytomas of all isotypes beside the ones the rabbit serum was specificly directed against. Before use, these sera were tested by immunoelectrophoresis against normal rat serum and rat IgM (IR473), IgA-(IR22), IgG1 (IR27), IgG2a (IR418), IgG2b (IR863), IgG2c (IR1148), IgD (IR731), and IgE (IR162) immunocytomas.

IgM DEPLETING TECHNIQUE

Mouse anti-rat IgM MoAb, MARM-7, was used to deplete serum IgM and therefore IgM XNA from adult rat sera. This MoAb was produced and purified by DEAE chromatography technique as described by Bazin et al. , MARM-7 was concentrated using a Minitan system (Millipore, Belgium) equipped with a 10,000 dalton filter, dialysed 3 times (24 h, 4° C.) agairist azide free PBS (pH 7.2) and then passed through 0.2 u sterile filter (Sartorius) to obtain a sterile solution at 3 mg/ml. MARM-7 was injected intraperitoneally in ether anesthetized rats. Individual blood samples were collected from the retroorbital plexus of ether anesthetized animals from day −3 to day 10 as indicated in the results section. Serum was obtained by centrifugation (700 g, 10 minutes), after coagulation of 1 ml blood samples, and stored at −20° C. or −70° C. until used.

ELISA TECHNIQUES AND MoAbS

Rat Igm seric concentrations. Briefly, 96 wells microtiter plates (Falcon) were coated overnight (16 h, 4° C.) with mouse anti-rat IgM MoAb (10 $\mu$g/ml) in 0.05M carbonate/bicarbonate buffer (pH 9.6). After saturation non-specific antigenic sites: (1 h, 37° C.) with 5% skimmed milk (Regilait) in PBS 0.1% Tween, microtiter plates were incubated with serial dilutions (1/100) of rat serum and IgM was detected by peroxidase labelled mouse, anti-rat kappa light chain, MoAb (MARK-1). Peroxidase labelled MARK-1 was revealed by Ortho-phenyldiamin (OPD, Sigma), 0.03% $H_2O_2$, (MERCK) in citrate buffer (pH 5.5) solution. Optical density was measured at 492 nm using an optical reader (MR 5000, Dinatecli). Purified rat IgM, LO-DNP-34, a rat hybridomas synthetizing anti-dinitrophenyl hapten MoAb was used as standard. In order to evaluate Igm serum concentration in treated rats, serial dilution (10 $\mu$g/ml of purified LO-DNP-34 was made and IgM serum concentration was measured after LOGIT transformation of standard and tested serum serial dilution curves. Two distinct ELISA tests were set up to measure total and free MARM-7 serum concentrations in treated animals. Total MARM-7 was defined as being the monoclonal mouse IgG1 (MARM-7) serum concentration detected in ELISA using two different rat anti-mouse IgG'1 MoAb recognizing distinct epitopes in the mouse IgG1 heavy chain. The ELISA technique used is identical to the one described above for the analysis of rat IgM serum concentrations. Briefly, 96 well microtiter plates were coated overnight (16 h, 4° C.) with rat anti-mouse IgG1 MoAb (LO-MG1-13) and rat serum dilutions (1/200) were revealed by peroxidase labelled rat anti-mouse IgG1 MoAb (LO-MG1-2-P). Total MARM-7 serum concentration was mesured after LOGIT transformation of both MARM-7 and rat serum serial dilution curves as described before. Free MARM-7 was defined as being the rat serum concentration of monoclonal mouse IgG1 (MARM-7) still able to recognize rat IgM in a ELISA test using peroxidase labelled LO-MG1-13 to reveal rat monoclonal IgM (LO-DNP-34)

bound MARM-7. The ELISA technique used was identical to the one described above for the analysis of rat IgM serum concentrations. Briefly, 96 well microtiter plates were coated overnight (16 h, 4° C.) with rat Igm MoAb (LO-DNP-34) and rat serum dilutions (1/100) were revealed by peroxidase labelled rat anti-mouse IgG1 MoAb (LO-MG1-13-P). Free MARM-7 serum concentration was measured after LOGIT transformation of both MARM-7 and rat serum serial dilutions curves as described before.

GUINEA PIG CELL CULTURE

Guinea pig cells were obtained by M199 (Gibco, Europe) 0.05% collagenase (from clostridium histolyticum, Boehringer/Mannheim) intraluminar digestion (10 min, 37° C.) of GP aorta. Cells were cultured in M199 medium (Gibco, Europe), 10% foetal calf serum (Biosys, France), 300 pg/ml glutamine (Gibco, Europe), 30% decomplemented GP serum (UCL, Belgium), 100 μg/ml streptomycin, 100 U/ml penicillin (Gibco, Europe) on 35 $mm_2$ plastic flasks (Falcon). Primary cultures reached confluence after 10 to 15 days. GP endothelial cells were identified by taking up of acetylated low density lipoproteines (DIL-AC-LDL) (Biomedical Technologies Co., USA) and by typical cobblestone morphological appearance after reaching confluence.

CELLULAR ELISA

Identification of IgM rat anti-guinea pig XAb was made by a cellular ELISA test adapted from Platt et al. and described by Soares et al. Binding of rat IgM XNA on guinea pig endothelial and smooth muscle cultured cells was revealed by peroxidase labelled MARM-4 MoAb.

COMPLEMENT HEMOLYTIC ACTIVITY

Complement hemolytic assays were achieved using as cellular targets SRBC previously sensitized with non agglutinating doses of rabbit anti SRBC polyclonal antibody. In CH50 assays sensitized SRBC (100 μl, $1 \times 10^8$ E/ml in $DGVB^{++}$ buffer) were incubated (60 minutes, 37° C.) with serially diluted rat serum samples (100 μl, $DGVB^{++}$ buffer). Hemolysis was stopped by addition of PBS (2.5 ml, pH 7.2) and optical density (414 nm) was measured from supernatants after centrifugation (2000 rpm, 7 minutes) of hemolysed SRBC, using an optical reader. 100% hemolysis was measured after incubation (60 minutes, 37° C.) of sensitized SRBC (100 μl, $1 \times 10^8$ E/ml in $DGVB^{++}$ buffer) with distilled water (100 μl). 0% hemolysis was measured after incubation (60 minutes, 37° C.) of sensitized SRBC with $DGVBY^+$ buffer (100 μl). Rat $C_{18}$, $C_2$, $C_3$, $C_4$ and $C_5$, dependent hemolytic activity were measured by the same method using sensitized SRSC ($1 \times 10^8$ E/ml in $DGVB^{++}$ buffer) previously incubated (at 4° C.) with respectively 1/50 $C_{18}$, $C_2$, $C_3$, $C_4$ or $C_5$ deficient sera. 0% and 100% SRBC hemolysis were measured in these assays using sensitized SRBC previously incubated (at 4° C.) with the respective deficient sera at the dilutions mentionned above. All rat sera analyses were made in duplicate.

HISTOLOGICAL PROCEDURES

For conventional histology, hearts were fixed by immersion in Bouin's fluid for 12 hours. Thick transversal sections of hearts were then dehydrated, embedded in paraffin and 6 μm-sections were applied onto gelatine and dried. Hemotoxylin Eosin Safran (HES) and Periodic Acid Shiff (PAS) stainings were performed for routine analyses and Phosphotungstic Hematoxylin (PTH) was achieved in order to analyze the presence of fibrin deposits and as an indicator of survival of cardiac myocytes (normal cardiac myocytes are "deep-blue" stained while slides previously coated with an aqueous solution of 0.3% (v/v) suffering cells are "light-blue" stained and death cells are red). For immunofluorescence, unfixed samples of rejected hearts were collected and thick transversal sections directly embedded in TissueTek II (Miles Scientific, IC, USA) and snapped-frozen in liquid nitrogen. Samples were stored at −70° C. until used. 8 um thick sections were applied onto slides and fixed in 70% (v/v) methanol for at least 5 hours. For immunolocalization, sections were first washed in PBS (pH 7.4) for 10 min and then quenched with 26.4 mM $NABH_4$, in PBS (10 min, room temp.). After PBS washing, sections were incubated (2 h, room temp.) with anti-rat IgM or anti-rat IgG2c rabbit antisera (1/100 in PBSA) or with fluoroscein coupled rabbit anti-rat C3 antiserum (1/100 in PBSA), washed (3 times, 30 min) in PBSA and incubated (30 min, room temp.) with fluorescein sheep coupled IgG anti-rabbit IgG (Organon Technika Corp., Durham, USA) (1/50) in PBSA and washed as mentioned above. Slides were covered with 2.5% (v/v) 1,4 diazo-2,2,2 octane (Janssen, Beerse, Belgium) in glycerol, and examined with a Zeiss Axiophot microscope equipped for epifluorescence (485 nm exciting filter, 520–560 nm barrier filter). Exposures were taken for 30–40 seconds on 400 ISO sensitive films (HP5 plus, Ilford, GB and Ektachrome 400, Kodak, USA). Negative controls, where first antibodies were replaced by a non relevant rabbit serum, showed no labelling.

In order to achieve total in vivo depletion of both circulating Igm and anti-guinea pig IgM XNA, adult LOU/C rats were intraperitoneally injected with 10 mg and 5 mg of MARM-7 at day −3 and day −1 respectively, prior to guinea pig cardiac xenotransplantation at day 0. Control animals were treated at the same days using equivalent volumes of PBS pH 7.2) and xenotransplanted at day 0.

Figure 6:
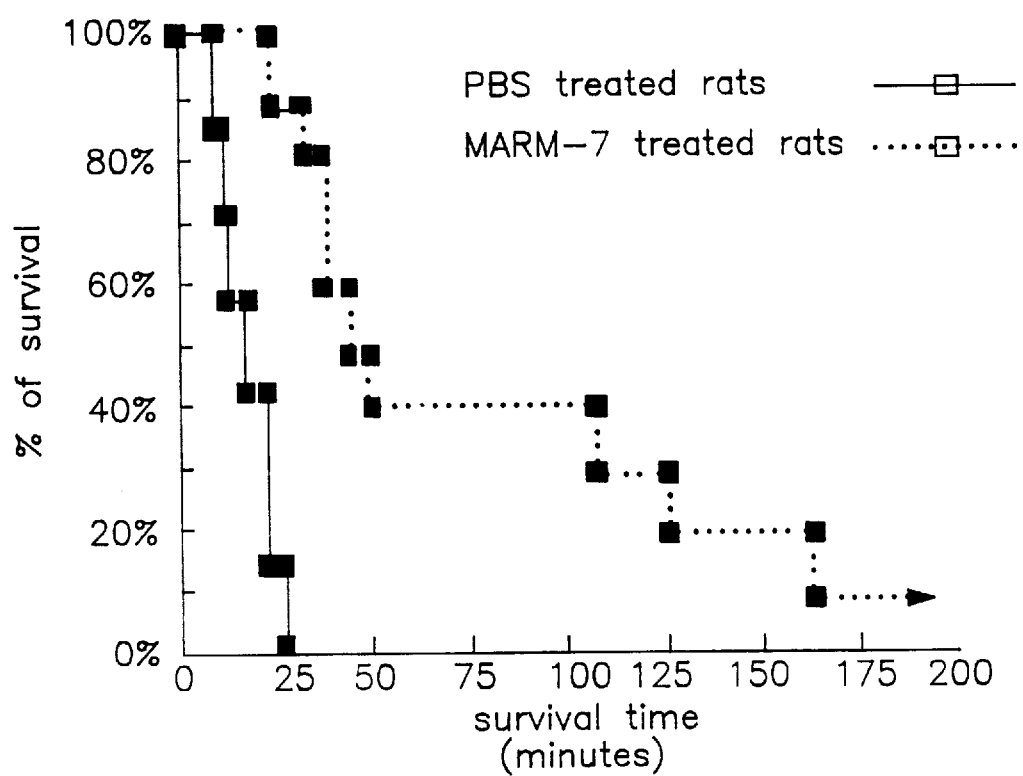
FIG. 6 depicts a comparison of the survival time in minutes of guinea pig cardiac xenografts in control rats and MARM7-treated rats.

As illustrated in FIG. 6, guinea pig cardiac xenografts survival time was strongly prolonged in MARM-7 treated rats (mean survival time of 62 minutes) compared to control rats (mean survival time of 18 minutes). A statistical analysis using Wilcoxon Rank test, showed that the prolongation of xenograft survival time in MARM-7 treated group was highly significant ($p<0.01$). Contrarily to control rats, an important variability on xenograft survival time was observed among MARM-7 treated rats. As well contrarily to control group, were 4 of 11 xenografts achieved had no primary function, all cardiac xenografts in the MARM-7 treated group had primary function.

Histological analysis of rejected guinea pig xenografts suggest that in both MARM-7 and PBS treated groups, cessation of coordinated cardiac contraction was due to hyperacute vascular rejection. No significant differences were observed, between the two groups, in the pathological aspects of rejected hearts, all showing typical HVR histopathology.

Figure 7A:
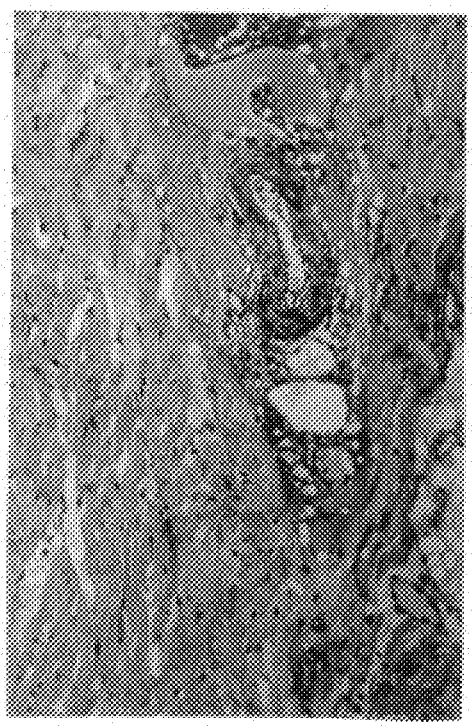
FIGS. 7a and 7b depict the histological condition of rejected guinea pig cardiac xenografts.
Figure 7B:

As shown in FIG. 7a and 7b, rejected cardiac xenografts revealed extensive edema surrounding large coronary vessels together with more or less important interstitial hemorrhage throughout the myocardium. Intraluminal vascular platelet aggregates were observed together with capillary and venular congestion, but microvascular thrombosis was not noticed. As suggested by the lack of typical staining with PTH, guinea pig cardiac muscle cells revealed to be under "metabolic sufferance" although necrosis could also be observed. None of the tissue samples analysed showed rat peripheral blood mononuclear cells infiltration through guinea pig myocardium. Exceptionally in one over 10

MARM-7 treated rats analysed, the rejected xenograft (survival time of more than 420 minutes) revealed an important polymorphonuclear and mononuclear cell infiltration but this observation may turn out not to be reproductible.

Figure 8:
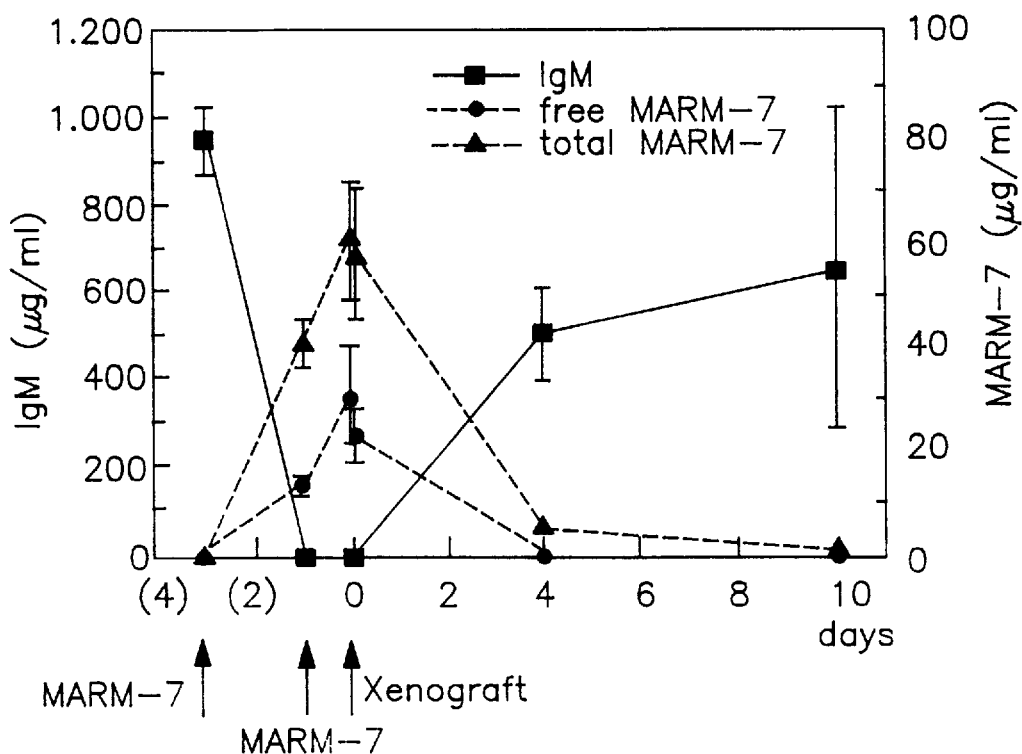
FIG. 8 shows the serum levels of IgM, free MARM7 and total MARM7 following MARM7 administration and xenograft transplantation.

As shown in FIG. 8, MARM-7 treated rats had undetectable levels of circulating IgM, 48 h after the first anti-Igm MoAb administration. Total IgM depletion was furthermore observed in these rats until the cardiac xenograft was performed. During the same period of time, high concentrations of "free MARM-7" and even higher concentration of "total MARM-7" were detected by ELISA suggesting that an important proportion of this MoAb was bound to circulating IgM in MARM-7/IgM immune complexes, not detectable by the ELISA test measuring rat IgM seric concentration. Consistent with the decrease of circulating "free MARM-7" between day 0 and day 10, Igm seric concentration increased to reach at day 10 post HVR pretreatment values. Contrary to MARM-7 treated rats no significant variation of circulating IgM was noticed on control rats (not illustrated).

Figure 9A:
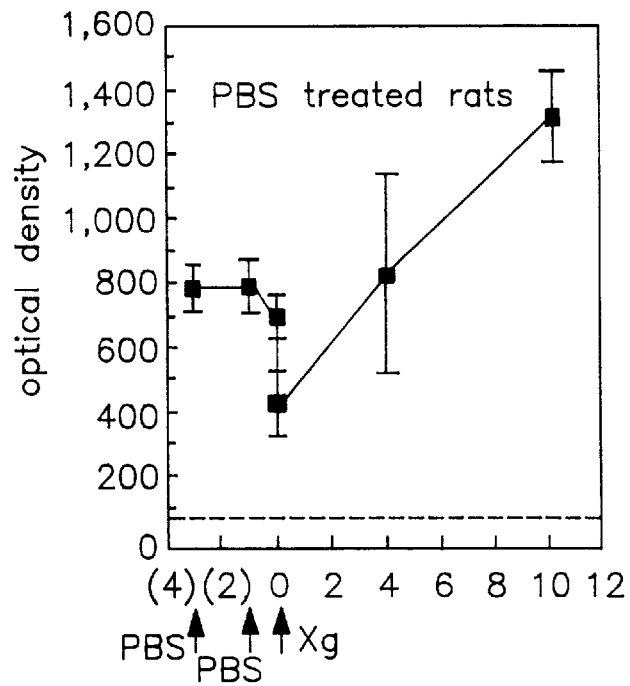
FIGS. 9a and 9b show the evolution of xenoreactive IgM natural antibodies in PBS and MARM7 treated animals.
Figure 9B:
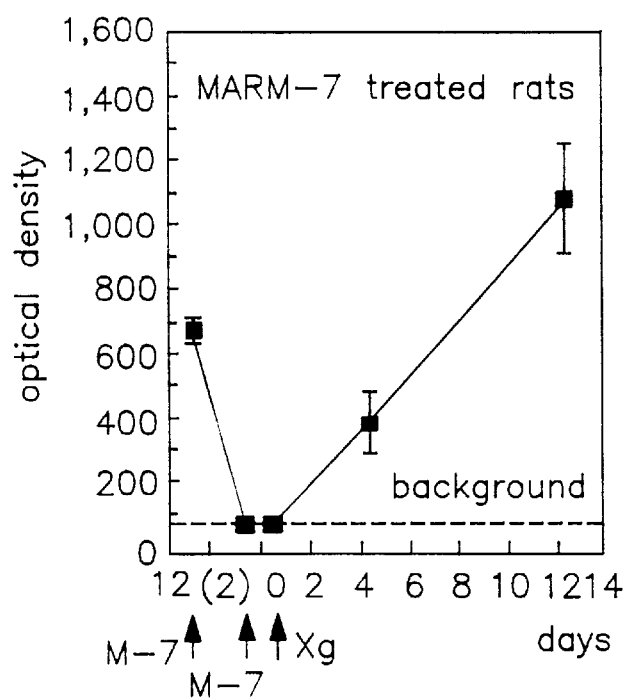

Shown in FIGS. 9a and 9b is the evolution of circulating IgM XNA in PBS and MARM-7 treated animals. In control rats, IgM XNA remained relatively unchanged between day −3 and day 0 before xenotransplantation. During xenograft hyperacute vascular rejection, a significant decrease of Igm XNA but not IgG2a XNA (not illustrated) seric levels was observed using a sensitive cellular ELISA previously described (Soares et al. 1992). In MARM-7 treated rats, as already noticed for IgM seric concentration (FIG. 10), total depletion of IgM XNA but not IgG2a XNA (not illustrated) was observed from day −1 to day 0. Specific IgM anti-guinea pig endothelial cells humoral immune response was observed from day 0 to day 10 post xenograft in both control and MARM-7 treated animals (FIGS. 9a and 9b). As illustrated in FIG. 10 no significant difference was observed between the two groups in $C_1q$ and $C_3$ dependent hemolytic complement activity, suggesting that MARM-7 injection and subsquent generation of MARM-7/IgM circulating immune complexes did not decrease complement activity. Both rat groups showed a similar decrease on $C_3$ activity during xenograft HVR. On the contrary, $C_1q$ and CH50 activity seems to be more decreased in PBS than in MARM-7 treated group.

The immunolocalization of rat IgM XNA, IgG2a XNA and $C_3$ deposits on rejected hearts is illustrated in FIG. 6. Specific binding of rat IgM XNA to guinea pig endothelial cells was observed in all the PBS treated rats analyzed. In correlation with the observation of edema and interstitial hemorrhage, IgM XNA were also detected throughout the myocardium and seemed to bind guinea pig cardiac muscle cells. In all MARM-7 treated rats analysed, IgM XNA were undetectable. IgG2a XNA were detected in both PBS and MARM-7 treated rats, without apparent specificity for the vascular xenogenic endothelium. $C_3$ deposits on xenograft vascular endothelium were observed in both rat groups. Moreover, interstitial hemorrhage and edema were correlated with extented $C_3$ deposition over guinea pig coronary vessels smooth muscle and endothelial cells as well as cardiac muscle cells in the myocardium.

Although the present invention, in a preferred embodiment, is directed to treating a patient to prevent or reduce the severity of xenograft rejection, it is to be understood that the scope of the invention is not limited thereto and is generally useful for removing or neutralizing natural human antibodies which are immunoreactive with antigens from a non-human species for any and all purposes.

Numerous modifications and variations of the present invention are possible in light of the above teachings and, therefore, within the scope of the appended claims, the invention may be practiced otherwise then as particularly described.

References:

(1) Bazin, H. Production of Rat Monoclonal Antibodies with LOU RAT Nonsecreting IR983F myeloma cell line. Prot. Biol. Fluids, 1982, Peeters Ed., 29th Colloquim 1981, Pergamon Press, Oxford and N.Y., pp. 615–18.

(2) Bazin, H.; Cormont, F.; DeClercq, L., Rat Monoclonal Antibodies II. Rapid and efficient method of purification from ascitic fluid or serum. J. Immunol. Neth. 1984, 71:9–16.

(3) Heron J. A. technique for accessory cervical heart transplantation in rabbits and rats. Acta Pathol. Microb. Scand., Section 79: 366, 1974.

(4) Olausson M., Mjornstedt L., Lindholm L., Brynger H. Non-suture organ grafting to the neck vessels in rats. Acta Clin. Scand. 150, 463–467, 1984.

What is claimed is:

1. A method of treatment against xenograft rejection in a human patient comprising the step of:

contacting in vivo the blood of said human patient with at least one antibody which specifically binds to human IgM in an amount effective for reducing blood levels of natural antibodies that are xenoreactive.

2. The method of claim 1 wherein the antibody is anti-human-$\mu$ chain antibody.

3. The method of claim 2 wherein the antibody is a monoclonal antibody.

4. The method of claim 3 wherein the contacting step is performed in vivo and the amount of the antibody is at least 25 mg.

5. The method of claim 3 wherein the contacting step is performed repeatedly over a number of days.

* * * * *